United States Patent
Gross et al.

(10) Patent No.: US 10,583,283 B2
(45) Date of Patent: Mar. 10, 2020

(54) RETINAL IMPLANT WITH IMAGE REGISTRATION

(71) Applicant: NANO-RETINA, INC., Wilmington, DE (US)

(72) Inventors: Yossi Gross, Moshav Mazor (IL); Yaakov Milstain, Zichron-Yaakov (IL); Leonid Yanovitz, Rishon Lezion (IL); Ofir Rimer-Cohen, Tal Shachar (IL)

(73) Assignee: NANO-RETINA, INC., Wilmington, DE (US)

( * ) Notice: Subject to any disclaimer, the term of this patent is extended or adjusted under 35 U.S.C. 154(b) by 213 days.

(21) Appl. No.: 15/884,941

(22) Filed: Jan. 31, 2018

(65) Prior Publication Data
US 2019/0232051 A1 Aug. 1, 2019

(51) Int. Cl.
*A61N 1/05* (2006.01)
*A61N 1/36* (2006.01)
(Continued)

(52) U.S. Cl.
CPC ....... *A61N 1/0543* (2013.01); *A61N 1/36046* (2013.01); *A61N 1/3787* (2013.01);
(Continued)

(58) Field of Classification Search
CPC . A61N 1/0543; A61N 1/3787; A61N 1/36046
(Continued)

(56) References Cited

U.S. PATENT DOCUMENTS

| 5,597,381 A | 1/1997 | Rizzo, III |
| 7,248,928 B2 | 7/2007 | Yagi |

(Continued)

FOREIGN PATENT DOCUMENTS

| DE | 10315397 | 10/2004 |
| DE | 10 2016 103 285 A1 | 8/2017 |

(Continued)

OTHER PUBLICATIONS

An Office Action dated May 16, 2018, which issued during the prosecution of U.S. Appl. No. 15/342,746.
(Continued)

*Primary Examiner* — Brian T Gedeon
*Assistant Examiner* — Philip C Edwards
(74) *Attorney, Agent, or Firm* — Sughrue Mion, PLLC

(57) ABSTRACT

Apparatus is provided including an intraocular device which is implanted entirely in an eye of a subject and includes photosensors which detect photons representing an image in a gaze direction of the subject, and stimulating electrodes which apply currents to the retina. The apparatus further includes an extraocular device including an imaging device which captures a wide-field image. The apparatus further includes processing circuitry which (i) receives the wide-field image from the imaging device of the extraocular device, (ii) receives a signal from the photosensors of the intraocular device, (iii) based on the signal from the photosensors, process the wide-field image from the imaging device to generate image data representative of a sub-portion of the wide-field image, and (iv) cause the electrodes to apply currents to the retina based on the image data. Other applications are also described.

15 Claims, 7 Drawing Sheets

(51) Int. Cl.
  *A61N 1/378* (2006.01)
  *A61F 9/00* (2006.01)
  *A61F 9/02* (2006.01)
  *A61F 9/08* (2006.01)

(52) U.S. Cl.
  CPC .............. *A61F 9/0017* (2013.01); *A61F 9/02* (2013.01); *A61F 9/08* (2013.01)

(58) Field of Classification Search
  USPC ........................................................ 607/54
  See application file for complete search history.

(56) References Cited

U.S. PATENT DOCUMENTS

| | | | |
|---|---|---|---|
| 7,957,810 | B2 | 6/2011 | Greenberg et al. |
| 8,150,526 | B2 | 4/2012 | Gross et al. |
| 8,428,740 | B2 | 4/2013 | Gefen et al. |
| 8,442,641 | B2 | 5/2013 | Gross et al. |
| 8,571,669 | B2 | 10/2013 | Liran et al. |
| 8,706,243 | B2 | 4/2014 | Gefen et al. |
| 8,718,784 | B2 | 5/2014 | Gefen et al. |
| 8,956,396 | B1 | 2/2015 | Friend et al. |
| 9,192,464 | B2 | 11/2015 | Liran et al. |
| 9,192,772 | B1 | 11/2015 | Tsukamoto et al. |
| 9,198,753 | B2 | 12/2015 | Gefen et al. |
| 9,265,945 | B2 | 2/2016 | Gross et al. |
| 9,314,626 | B2 | 4/2016 | McDremott et al. |
| 9,331,791 | B2 | 5/2016 | Liran et al. |
| 9,370,417 | B2 | 6/2016 | Gefen |
| 9,474,902 | B2 | 10/2016 | Gefen et al. |
| 9,566,191 | B2 | 2/2017 | Gefen et al. |
| 2003/0014089 | A1 | 1/2003 | Chow et al. |
| 2004/0039401 | A1 | 2/2004 | Chow et al. |
| 2004/0054407 | A1 | 3/2004 | Tashiro et al. |
| 2004/0078064 | A1 | 4/2004 | Suzuki |
| 2005/0090875 | A1 | 4/2005 | Palanker et al. |
| 2005/0165409 | A1 | 7/2005 | Eckmiller |
| 2005/0168569 | A1 | 8/2005 | Igarashi et al. |
| 2006/0116743 | A1 | 6/2006 | Gibson et al. |
| 2006/0224212 | A1 | 10/2006 | Kennedy |
| 2009/0216295 | A1 | 8/2009 | Zrenner et al. |
| 2010/0204754 | A1* | 8/2010 | Gross ............... A61N 1/36046 607/53 |
| 2012/0035726 | A1 | 2/2012 | Gross et al. |
| 2012/0065704 | A1 | 3/2012 | Kavasssery et al. |
| 2012/0194781 | A1 | 8/2012 | Agurok |
| 2012/0239126 | A1 | 9/2012 | Zhou et al. |
| 2012/0259410 | A1* | 10/2012 | Gefen ...................... A61F 2/14 623/6.11 |
| 2014/0046418 | A1 | 2/2014 | Williams et al. |
| 2014/0143559 | A1 | 5/2014 | Liran et al. |
| 2015/0342723 | A1 | 12/2015 | Abramson et al. |
| 2016/0099046 | A1 | 4/2016 | Liran |
| 2016/0220828 | A1 | 8/2016 | Yan Poon et al. |
| 2017/0368351 | A1 | 12/2017 | Liran |
| 2018/0071146 | A1 | 3/2018 | Liran et al. |
| 2018/0117329 | A1 | 5/2018 | Degtiar et al. |
| 2018/0117330 | A1 | 5/2018 | Weinberger et al. |
| 2019/0046798 | A1 | 2/2019 | Kindt et al. |

FOREIGN PATENT DOCUMENTS

| | | |
|---|---|---|
| WO | 2010/089739 | 8/2010 |
| WO | 2011/086545 | 7/2011 |
| WO | 2012/017426 | 2/2012 |
| WO | 2012/114327 | 8/2012 |
| WO | 2012/153325 | 11/2012 |
| WO | 2013049890 A1 | 4/2013 |
| WO | 2014/080343 | 5/2014 |
| WO | 2014/141089 | 9/2014 |
| WO | 2015/101932 | 7/2015 |
| WO | 2015/110933 | 7/2015 |
| WO | 2017210730 A1 | 12/2017 |
| WO | 2018184837 A1 | 10/2018 |

OTHER PUBLICATIONS

An Office Action dated Apr. 27, 2018, which issued during the prosecution of U.S. Appl. No. 15/342,765.
An Office Action dated Jun. 14, 2018, which issued during the prosecution of U.S. Appl. No. 15/195,212.
An International Search Report and a Written Opinion both dated May 4, 2018, which issued during the prosecution of Applicant's PCT/IL2017/051202.
Pham et al. Self Closing corneoscleral tunnel incision in cataract surgery, Opthalmaloge. Feb. 1996;93(1):8-1 1.
Yang et al. Surgical results of pars plana vitrectomy combined with phacoemulsification J Zhejian Univ Science B 20067(2):129-132.
International Search Report and Written Opinion dated Apr. 2, 2019 from the International Searching Authority in counterpart International Application No. PCT/IL2019/050059.
An Invitation to Pay Additional Fees issued in International Appl. PCT/IL2017/051202, dated Feb. 16, 2018.
A Final Office Action issued in U.S. Appl. No. 15/195,212, dated Feb. 23, 2018.

\* cited by examiner

RETINAL IMPLANT WITH IMAGE REGISTRATION

FIELD OF THE INVENTION

The present invention relates generally to implantable medical devices, and specifically to a retinal prosthesis.

BACKGROUND

Retinal malfunction, due to degenerative retinal diseases, is a leading cause of blindness and visual impairment. Implantation of a retinal prosthesis is a technology for restoring some useful vision in individuals suffering from retina-related blindness.

The retina is a multi-layered light-sensitive structure that lines the posterior, inner part of the eye. The retina contains photoreceptor cells, rods and cones, which capture light and convert light signals into neural signals transmitted through the optic nerve to the brain. Rods are responsible for light sensitive, low resolution black and white vision, whereas cones are responsible for sharp, high resolution color vision.

There are several types of retinal implants. For example, suprachoroidal implants are placed between the sclera and choroid of the eye. Additional types of retinal implants are epiretinal implants, which are placed on top of the retinal surface, and subretinal implants, which are placed under the retina between the photoreceptor layer and the retinal pigment epithelium, directly stimulating retinal cells and relying on the normal processing of the inner and middle retinal layers. Epiretinal designs typically include an electrode array directly stimulating ganglion cells and bypassing other retinal layers.

Some retinal implants include an internal imager, i.e., an intraocular camera. The internal imager effectively replaces the functionality of the native photoreceptor cells by capturing a scene in the direction of a subject's gaze.

In other cases, retinal implants rely on an external camera for capturing the visual information and replacing the functionality of the native photoreceptor cells.

SUMMARY OF THE INVENTION

In some applications of the present invention, apparatus is provided for restoring at least partial vision in a subject suffering from a retinal disease. The apparatus typically comprises an extraocular imaging device, i.e., a camera, for capturing visual information. The extraocular device typically comprises an eyeglasses frame that is placed in front of the subject's eye, and the extraocular imaging device is coupled to the eyeglasses frame. The apparatus is typically sensitive to eye movements of the subject by detecting a direction of the subject's gaze, such that—even though an extraocular imaging device is imaging the scene—the subject is nevertheless generally not required to move his head in order to capture an image in the direction of his gaze. Typically, the apparatus described herein comprises an intraocular device, in addition to the extraocular device. In accordance with some applications of the present invention, the intraocular apparatus comprises an intraocular imaging device.

The intraocular device is implanted entirely in the subject's eye, typically, in an epiretinal position. The intraocular device comprises an energy receiver, which receives a beam of light from a power source to power components of the intraocular device. For some applications, the intraocular device further comprises an array of photosensors, a plurality of stimulating electrodes, and driving circuitry which utilizes the energy from the energy receiver to drive the electrodes to apply currents to a retina. Stimulation of the retina elicits action potentials in the retinal ganglion cells, restoring some vision by activating the intact mechanisms of the eye.

The extraocular device typically further comprises the power source, for example a laser, that is coupled to the eyeglasses frame and is configured to emit the beam of light toward the subject's eye. The beam of light is typically outside the visible range, e.g., outside 380-750 nm. For example, the power source may be configured to emit the beam of light in the range of 750-900 nm.

Typically, the extraocular imaging device comprises a wide-angle lens that captures a wide-field image. However, only a sub-portion of the wide-field image captured by the imaging device actually corresponds to objects in a gaze direction of the subject. For example, the subject's head (and eyeglasses) may be facing forward, while his eyes may be facing left. Therefore, only a sub-portion of the wide-field image captured by the extraocular imaging device actually corresponds to objects to the left of the subject, in the subject's gaze direction. As provided by some applications of the present invention, the externally-captured image is processed by the apparatus in order to generate a processed image that correlates with the gaze direction of the subject. The stimulating electrodes are then driven to apply currents to the retina based on the processed image.

Processing of the externally-captured image to correspond to the changing gaze direction of the subject is typically performed based on communication between the extraocular device and the intraocular device.

For example, for some applications, the array of photosensors function as an intraocular imager and are configured to capture an ambient image in a gaze direction of the subject. The image data, or data regarding features of the image are transferred from the intraocular device to the extraocular device, and the gaze direction of the subject is determined by the extraocular device based on the image data, by comparing the transmitted image data to the externally-captured image. The wide-field image captured by the extraocular imaging device is then cropped based on the determination of the gaze direction. For some applications, the cropped image is larger than what was visible to the intraocular imager, such that the synergetic operation of the intraocular imager and the extraocular imager allow the subject to see a wider field of view than would have been possible using only the intraocular imager. Alternatively or additionally, the processed image that is derived from the externally-captured image is of higher quality than that available based on data from the photosensors in the intraocular device.

In another application, the array of photosensors is sensitive to the non-visible beam of light emitted from the power source which is attached to the extraocular device. Typically, the gaze direction of the subject, in such applications, is determined based on an intensity of the non-visible beam of light on various ones of the photosensors in the array of photosensors. The wide-field image captured by the extraocular imaging device is then cropped based on the determination of the gaze direction.

There is therefore provided in accordance with some applications of the present invention, apparatus, including:

(A) an intraocular device configured to be implanted entirely in a subject's eye, the intraocular device including:

an energy receiver configured to receive light to power the intraocular device;

a plurality of stimulating electrodes; an array of photosensors, each photosensor configured to detect photons representing an image in a gaze direction of the subject, and to generate a signal in response thereto; and driving circuitry configured to utilize energy from the energy receiver to drive the electrodes to apply currents to a retina of the subject's eye;

(B) an extraocular device including:

an eyeglasses frame, configured to be placed in front of the subject's eye;

a non-visible light source coupled to the eyeglasses frame and configured to transmit light to the energy receiver;

an imaging device coupled to the eyeglasses frame and configured to capture a wide-field image; and (C) processing circuitry configured to (i) receive the wide-field image from the imaging device, (ii) based on the signal from the photosensors, process the wide-field image from the imaging device to generate image data representative of a sub-portion of the wide-field image, and (iii) cause the driving circuitry to drive the electrodes to apply currents to the retina based on the image data.

For some applications, the extraocular device is configured to modulate the light emitted from the non-visible light source to contain data representative of the image captured by the imaging device.

For some applications, the imaging device includes a wide-angle lens.

For some applications, the imaging device is configured to capture a field of view that is larger than a field of view detected by the array of photosensors.

For some applications, the imaging device is positioned with respect to the eyeglasses frame such that when the subject wears the eyeglasses frame, the image detected by the array of photosensors is a sub-portion of the wide-field image captured by the imaging device.

For some applications, the sub-portion of the wide-field image generated by the processing circuitry is derived from a field of view that is larger than a field of view detected by the array of photosensors.

For some applications, the intraocular device further includes an image processor, configured to extract one or more principle features of the image detected by the array of photosensors, and the processing circuitry is configured to generate the image data representative of the sub-portion of the wide-field image based on the extracted principle features of the image detected by the array of photosensors.

For some applications, the extraocular device includes the processing circuitry and is configured to transmit the image data representative of the sub-portion of the wide-field image to the intraocular device to cause the driving circuitry to drive the electrodes to apply currents to the retina based on the image data.

For some applications, the intraocular device includes the processing circuitry.

There is further provided in accordance with some applications of the present invention, apparatus, including:

(A) an extraocular device, including:

an eyeglasses frame, configured to be placed in front of an eye of a subject;

a non-visible light source coupled to the eyeglasses frame and configured to emit toward the eye a beam of light that (i) is outside of 380-750 nm, and (ii) does not contain data representative of an image; and an imaging device coupled to the eyeglasses frame and configured to capture a wide-field image;

(B) an intraocular device configured to be implanted entirely in the subject's eye, the intraocular device including:

an energy receiver, configured to receive the beam of light from the non-visible light source to power the intraocular apparatus;

a plurality of stimulating electrodes; driving circuitry configured to utilize energy from the energy receiver to drive the electrodes to apply currents to a retina of the subject's eye; and an array of photosensors, configured to receive the beam of light from the power source and to generate a signal in response to a parameter of the beam of light, the parameter being indicative of a gaze direction of the subject; and (C) processing circuitry configured to (i) receive the wide-field image from the imaging device, (ii) based on the signal from the photosensors, process the wide-field image from the imaging device to generate image data representative of a sub-portion of the wide-field image, the sub-portion corresponding to an image that is in the gaze direction of the subject and (iii) cause the driving circuitry to drive the electrodes to apply currents to the retina based on the image data.

For some applications, the extraocular device includes the processing circuitry and is configured to transmit the image data representative of the sub-portion of the wide-field image to the intraocular device to cause the driving circuitry to drive the electrodes to apply currents to the retina based on the image data.

For some applications, the intraocular device includes the processing circuitry.

For some applications, the imaging device includes a wide-angle lens.

For some applications, the array of photosensors are generally insensitive to visible light.

For some applications, the parameter of the beam of light includes an intensity of the beam of light, and the photosensor array is configured to generate a signal in response to the intensity of the beam of light received by the photosensor array.

There is further provided in accordance with some applications of the present invention, a method including:

capturing a wide-field image by using an extraocular imaging device coupled to an eyeglasses frame which is positioned in front of an eye of a subject;

detecting photons representative of an image in a gaze direction of the subject by using an intraocularly implanted array of photosensors;

using processing circuitry, processing the wide-field image from the extraocular imaging device, based on the image detected by the implanted array of photosensors, to generate image data representative of a sub-portion of the wide-field image, the sub-portion of the wide-field image being in the gaze direction of the subject; and using driving circuitry, driving electrodes to apply currents to a retina of the eye based on the image data.

For some applications, using the processing circuitry includes using processing circuitry electrically coupled to the array of photosensors.

For some applications, using the processing circuitry includes using processing circuitry electrically coupled to the imaging device.

There is further provided in accordance with some applications of the present invention, a method including:

capturing a wide-field image by using an extraocular imaging device coupled to an eyeglasses frame which is positioned in front of an eye of a subject;

emitting toward the eye, a beam of light that (i) is outside of 380-750 nm, and (ii) does not contain data representative of an image;

receiving the beam of light by an array of intraocularly implanted array of photosensors such that a parameter of the beam of light is indicative of a gaze direction of the subject;

using processing circuitry, processing the wide-field image from the extraocular imaging device based on the parameter of the beam of light, to generate image data representative of a sub-portion of the wide-field image, the sub-portion of the wide-field image being in the gaze direction of the subject; and using driving circuitry, driving electrodes to apply currents to a retina of the eye based on the image data.

For some applications, using the processing circuitry includes using processing circuitry electrically coupled to the array of photosensors.

For some applications, the processing circuitry includes using processing circuitry electrically coupled to the imaging device.

The present invention will be more fully understood from the following detailed description of applications thereof, taken together with the drawings, in which:

DETAILED DESCRIPTION OF EMBODIMENTS

Figure 1:
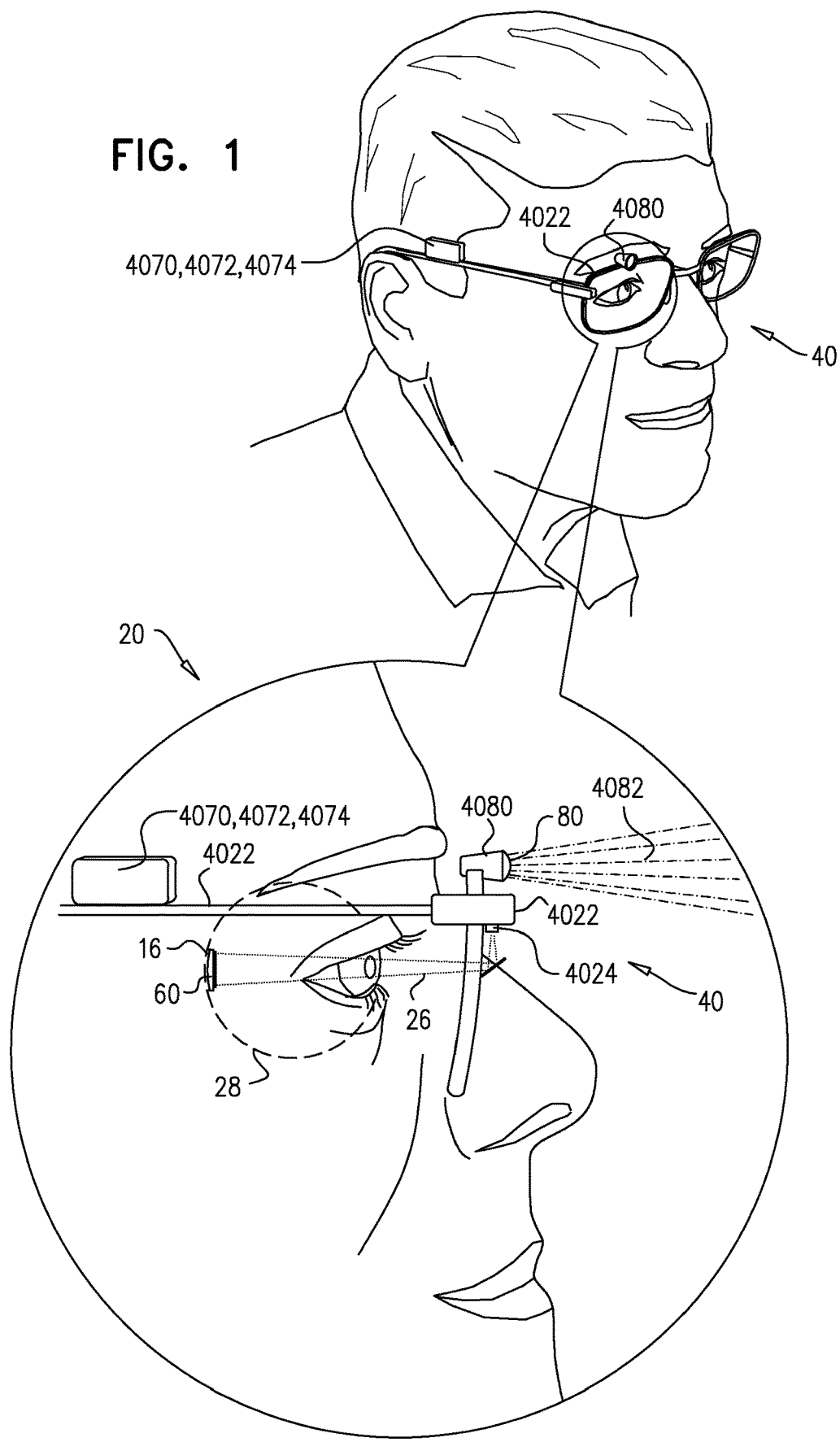
FIG. 1 is a schematic illustration of apparatus for restoring at least partial vision in a subject, in accordance in accordance with some applications of the present invention.

Reference is made to FIG. 1, which is a schematic illustration of apparatus 20 for restoring at least partial vision in a subject, in accordance with some applications of the present invention. Apparatus 20 comprises an extraocular device 40 and an intraocular device 60.

Extraocular device 40 typically comprises an eyeglasses frame 4022, configured to be placed in front of an eye 28 of a subject, and a power source, typically a non-visible light source 4024, coupled to the eyeglasses frame and configured to emit an infrared light beam 26 toward eye 28 of the subject. Additionally, coupled to eyeglasses frame 4022, is an imaging device 4080 which typically comprises a wide-angle lens 80 which captures a wide-field image of the subject's environment (indicated by light rays 4082).

Figure 3:
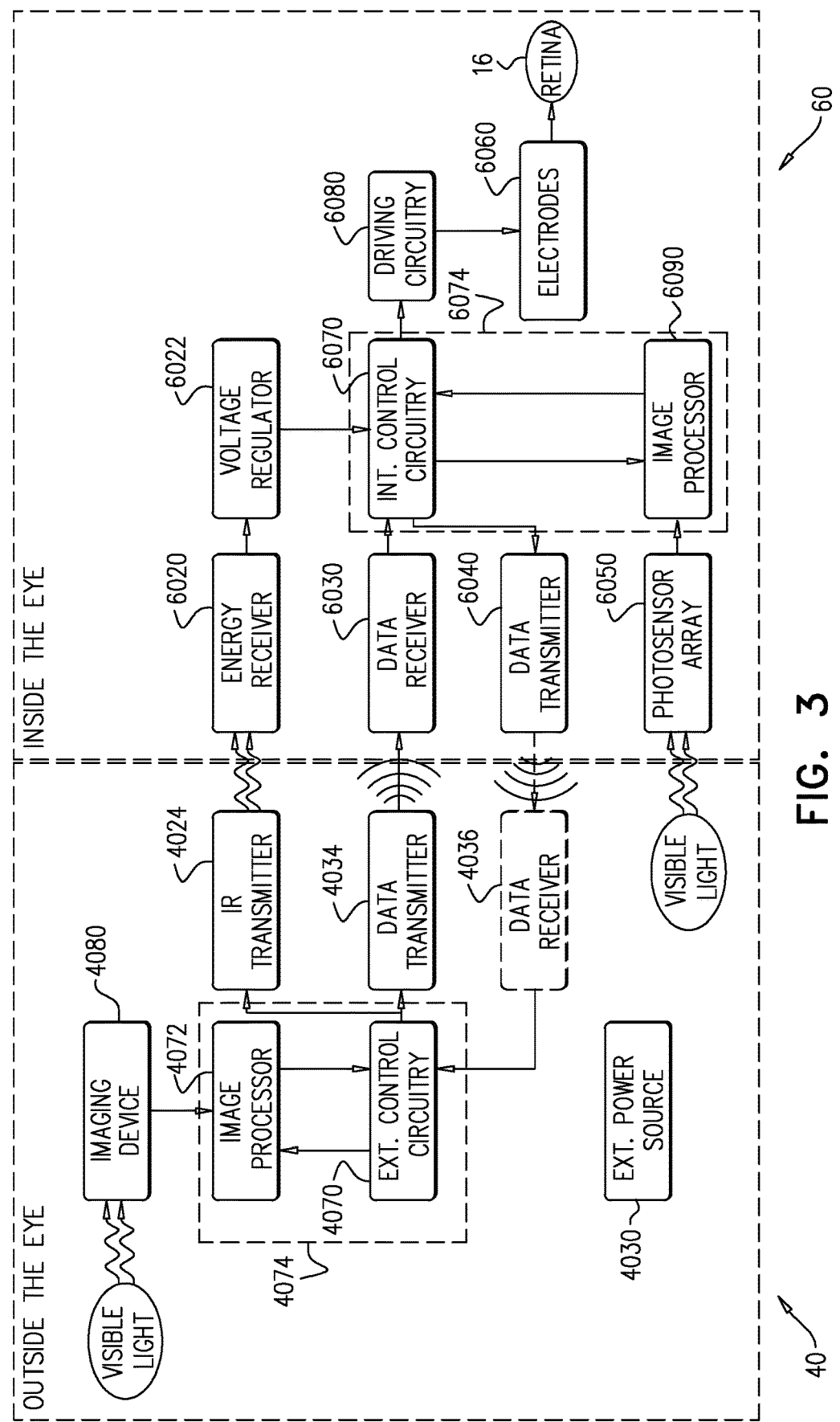
FIG. 3 is a block diagram of the transmission of energy and the processing of image data in the apparatus for restoring vision, in accordance with some applications of the present invention.
Figure 5:
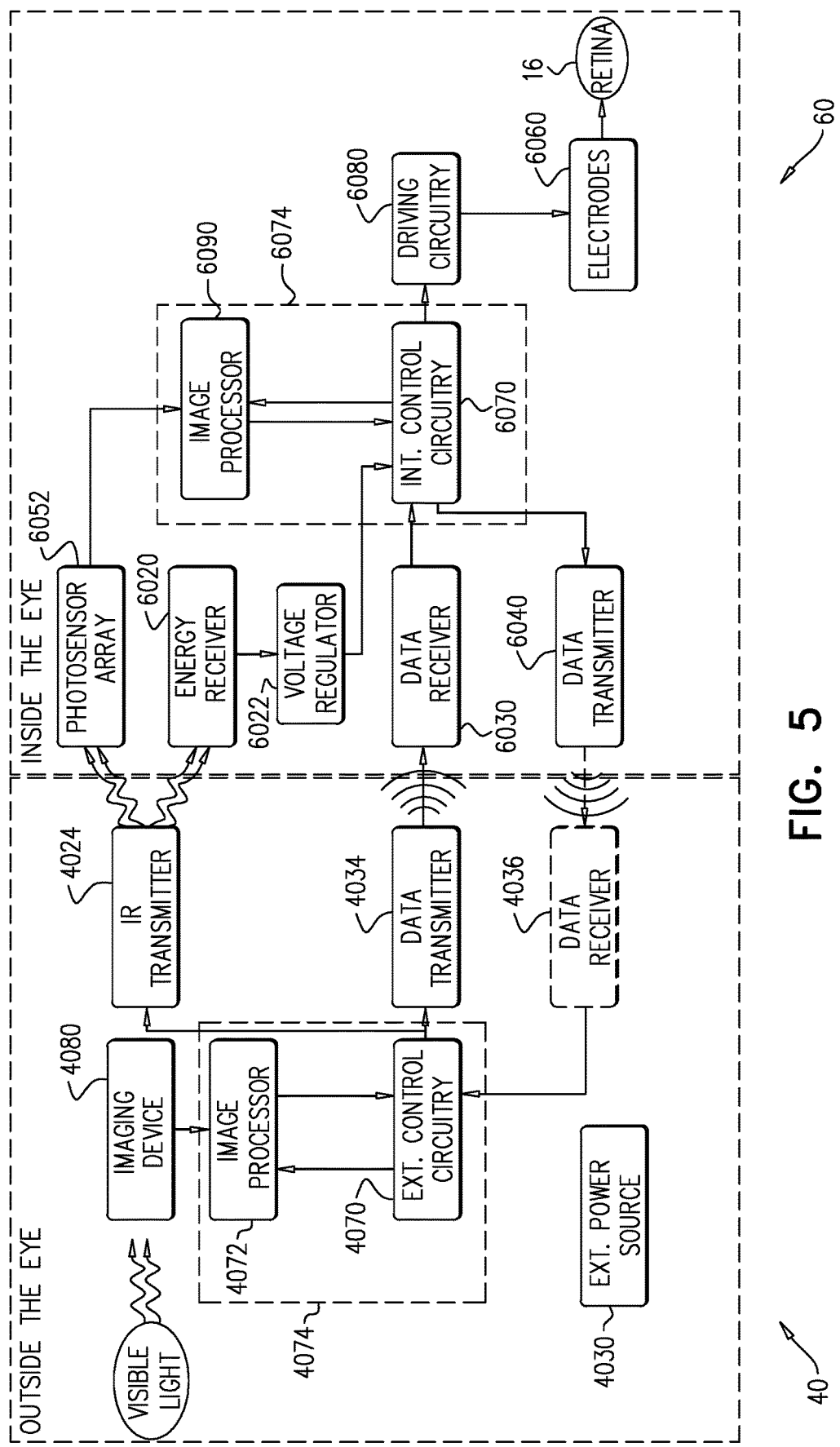
FIG. 5 is a block diagram of the transmission of energy and the processing of image data in the apparatus for restoring vision, in accordance with some applications of the present invention.

Intraocular device 60 is implanted entirely in eye 28, typically, in an epiretinal position. Intraocular device 60 comprises an energy receiver 6020 (FIGS. 3 and 5), which receives light beam 26 from power source 4024 to power components of intraocular device 60. Intraocular device 60 further comprises a photosensor array comprising a plurality of photosensors, a plurality of stimulating electrodes, and driving circuitry configured to utilize the energy from the energy receiver to drive the electrodes to apply currents to the retina (components of intraocular device 60 are illustrated in FIGS. 3 and 5). Stimulation of the retina elicits action potentials in the retinal ganglion cells, restoring some vision by activating the intact mechanisms of the eye.

In general, apparatus 20 captures the wide-field image using imaging device 4080 and processes the wide-field image such that only a representation of a sub-portion of the wide-field image (the sub-portion being the portion of the image that is in the gaze direction of the subject) is ultimately applied to the retina by the electrodes of intraocular device 60.

Processing of the wide-field image into a sub-portion of the image that corresponds to an image in the gaze direction of the subject is typically accomplished by communication between extraocular device 40 and intraocular device 60 as described herein below with reference to FIGS. 2A-5.

Reference is now made to FIGS. 2A-C and FIG. 3, which depict apparatus 20 in accordance with some applications of the present invention. More specifically, in the applications described with reference to FIGS. 2A-3, apparatus 20 performs image registration in which two separate sets of image data (one from extraocular imaging device 4080 and another from internal imaging photosensor array 6050) are integrated into a coordinate system.

Figure 2A:
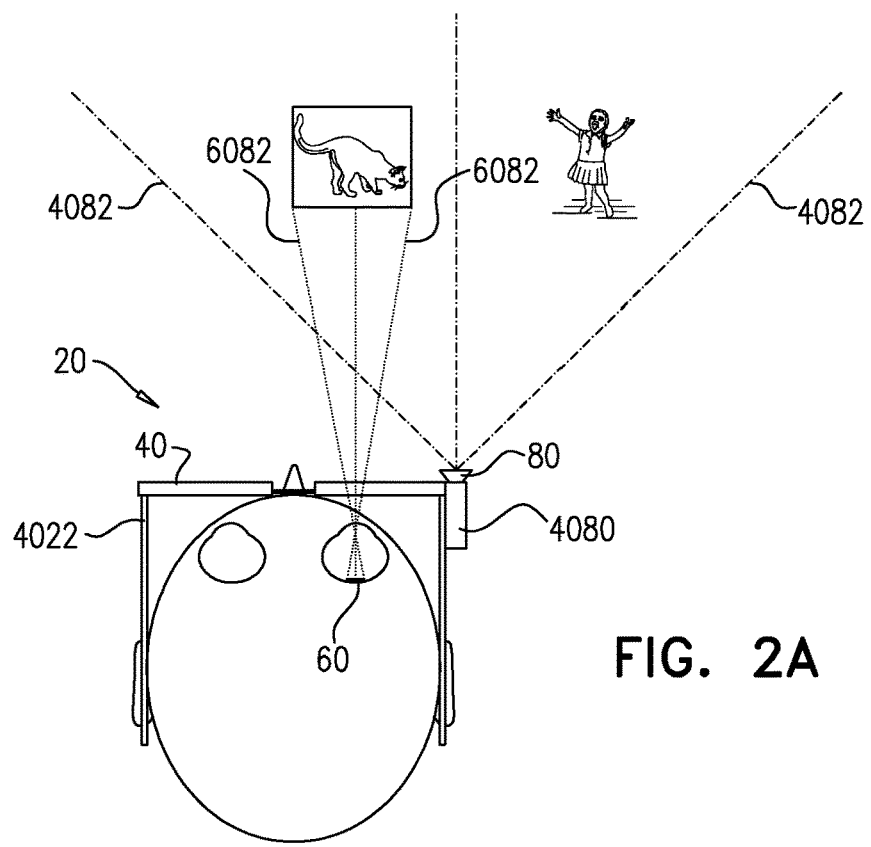
FIGS. 2A-C are schematic illustrations of apparatus for restoring at least partial vision in a subject, in accordance in accordance with some applications of the present invention.
Figure 2B:
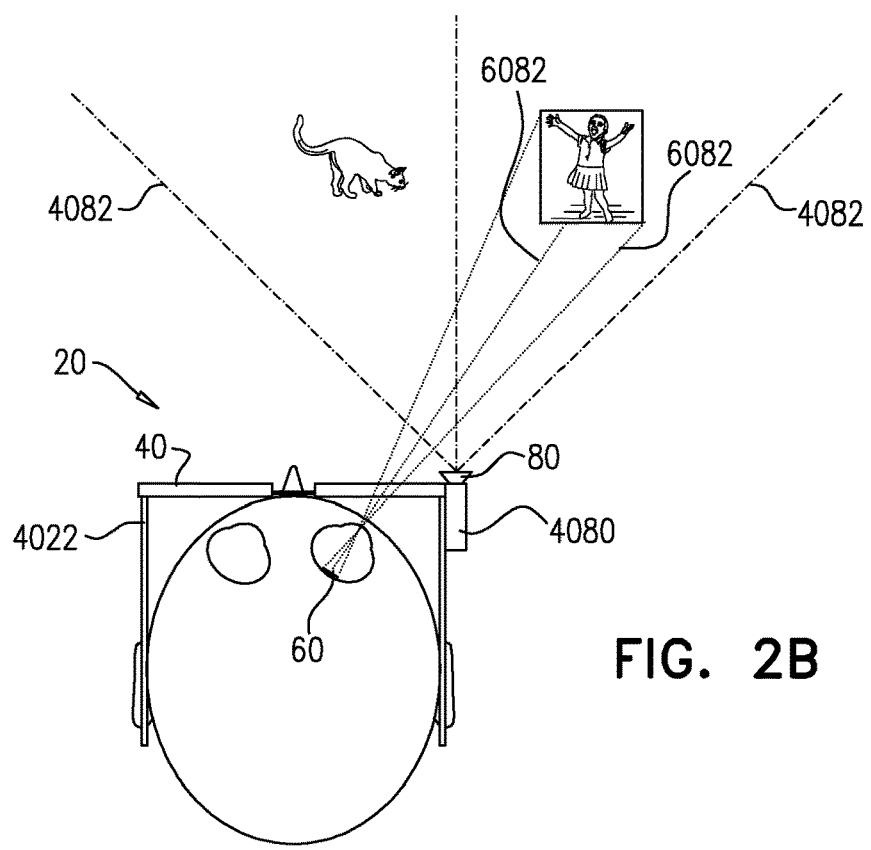

Reference is first made to FIGS. 2A-B. As described hereinabove with reference to FIG. 1, apparatus 20 comprises an extraocular device 40 and an intraocular device 60. Extraocular device 40 comprises imaging device 4080 which typically captures a wide field of view (FOV), i.e., a wide field image, that is in the subject's environment. It is noted that although there are typically movements of eye 28, these eye movements do not change the field of view of imaging device 4080. The wide field of view captured by imaging device 4080 is represented by rays 4082 in FIGS. 2A-B.

Independently of external imaging device 4080, photosensor array 6050 of intraocular device 60 captures a visual scene represented by rays 6082. Photosensor array 6050 is typically an intraocular imager that is implanted on retina 16 of the subject as part of implantable intraocular device 60, to replace the functionality of the native photosensor cells. Placing the imager intraocularly typically mimics the natural visual path, and as such supports natural ocular phenomena, for example, eye movement.

Since intraocular device 60 is typically fixed to retina 16, photosensor array 6050 is typically affected by movements of eye 28 such that the visual scene captured by photosensor array 6050 is a visual scene in a gaze direction of the subject. Due to implant-size limitations, photosensor array 6050 typically captures a field of view that is smaller than the field of view captured by external imaging device 4080. As shown in FIGS. 2A-B, the image captured by photosensor array 6050 and indicated by rays 6082, is a sub-portion of the wide field image captured by imaging device 4080 and indicated by rays 4082. Typically, rays 6082 represent a visual scene that is in the direction of the gaze of the subject, therefore representing a region of interest to the subject.

Apparatus 20 performs an image registration process using the two separate sets of data (i.e., the image captured by imaging device 4080 and the image captured by photosensor array 6050) to generate a unified coordinate system, essentially achieving the same functionality as an eye tracking system which provides information regarding a gaze direction of the subject. Thus, the image from imaging device 4080 may be cropped in accordance with the gaze direction of the subject to include a sub-portion of the wide-field image that is in the gaze direction of the subject. The data from the processed image from imaging device 4080 is subsequently transmitted to intraocular device 60 such that electrodes 6060 apply currents to retina 16 based on the processed image from extraocular device 40.

Figure 2C:
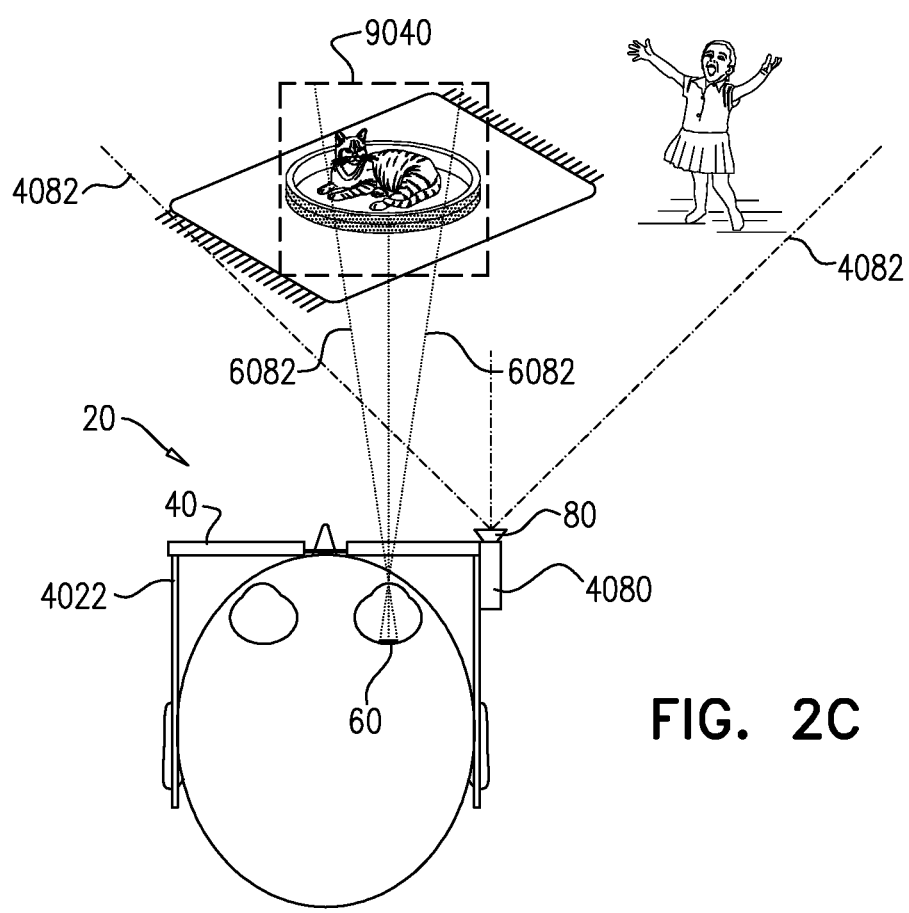

Reference is now made to FIG. 2C. Typically, the processed image that is derived from extraocular imaging device 4080 is of a wider field of view than that available based on data from photosensor array 6050 in intraocular device 60. As shown in FIG. 2C and described hereinabove with reference to FIGS. 2A-B, the image captured by photosensor array 6050 and indicated by rays 6082, is a sub-portion of the wide field image captured by imaging device 4080 and indicated by rays 4082. Typically, rays 6082 represent a visual scene captured by photosensor array 6050 and in the direction of the gaze of the subject, therefore representing a region of interest to the subject. However, due to implant-size limitations, photosensor array 6050 typically captures a relatively small field of view in the gaze direction of the subject.

As described herein, apparatus 20 performs an image registration process using two separate sets of data (i.e., the image captured by imaging device 4080 and the image captured by photosensor array 6050) to generate a processed image of the externally-captured image. As described hereinabove and shown in FIG. 2C, the processed image includes a sub-portion of the wide-field image captured by extraocular imaging device 4080 (indicated by rays 4082). Additionally, as shown in FIG. 2C, the processed image derived from the extraocular imaging device 4080, indicated by box 9040, is of a wider field of view than that of photosensor array 6050, indicated by rays 6082. Electrical stimulation based on the data from the processed image from imaging device 4080 is subsequently applied to retina 16, thus providing an enhanced sensation of an image by combining advantages of both an extraocular imager and an intraocular imager. Namely, providing a sensation of an image that is both (a) in a region of interest to the subject, and (b) is of a larger field of view and higher quality than would have been possible using only the intraocular imager.

Reference is now made to FIG. 3, which is a block diagram of the transmission of energy and image data between extraocular device 40 and intraocular device 60 to achieve image registration in apparatus 20, in accordance with some applications of the present invention.

As shown and described hereinabove with reference to FIGS. 1 and 2A-B, extraocular device 40 comprises imaging device 4080 which is configured to capture a wide field of view (FOV).

Extraocular device 40 additionally comprises a power source, shown as IR transmitter 4024. IR transmitter 4024 is typically a laser which emits beam of light 26 to power components of intraocular device 60. Beam of light 26 is typically outside of the visible light range, e.g., outside 380-750 nm. Beam of light transmitted to intraocular device 60 is received by energy receiver 6020. Intraocular device 60 additionally comprises a voltage regulator 6022 configured to maintain a generally constant voltage level to power the components of intraocular device 60.

Intraocular device 60 further comprises photosensor array 6050 which comprises a plurality of photosensors. Photosensor array 6050 detects photons of visible light and by doing so, captures a visual scene in a gaze direction of the subject (as noted above, since photosensor array 6050 is placed and secured within the eye, the subject can naturally scan a scene by moving his eyes). The image captured by photosensor array 6050 is typically transmitted upstream to extraocular device 40 via data transmitter 6040, for registration with the image captured by imaging device 4080 as described hereinabove. For some applications, instead of the entire image captured by photosensor array 6050 being transmitted to extraocular device 40, the image is processed by processing circuitry 6074 of intraocular device 60 (in particular the image is processed by an image processor 6090 of intraocular device 60) so that principle features are extracted from the image (such as straight lines, or areas of high contrast). The set of features is then transmitted via data transmitter 6040 to extraocular device 40 for registration with the image captured by imaging device 4080. The image data from data transmitter 6040 (the captured image or the features of the image) are received in extraocular device 40 by data receiver 4036 and transferred to processing circuitry 4074 in extraocular device 40. In particular, the image data is processed by extraocular control circuitry 4070 and image processor 4072 for registration with the image captured by imaging device 4080. Based on the image data from intraocular device 60, the wide field image captured by imaging device 4080 is processed by image processor 4072. The image data from intraocular device 60 provides information regarding the gaze direction of the subject, and based on that information, the image captured by imaging device 4080 is cropped such that a sub-portion of the wide-field image which is in the gaze direction of the subject is included in the cropped image. The processed image is transmitted back to intraocular device 60 via data transmitter 4034 and received in intraocular device 60 by data receiver 6030 and intraocular control circuitry 6070. Control circuitry 6070 transmits data in response to the received processed image to driving circuitry 6080, which in turn drives electrodes 6060 to apply currents to retina 16.

Reference is still made to FIG. 3. For some applications, total image data of the image captured by extraocular imaging device 4080 are transmitted downstream to intraocular device 60 via data transmitter 4034, for registration with the image captured by photosensor array 6050.

For such applications, the image data from data transmitter 4034 are received in intraocular device 60 by data receiver 6030 and transferred to processing circuitry 6074 in intraocular device 60 for processing. In particular, the image data are processed by intraocular control circuitry 6070 and image processor 6090 for registration with the image captured by photosensor array 6050. Based on registration of the data from the extraocular device 4080 and intraocular photosensor array 6050, the wide field image captured by imaging device 4080 is cropped by image processor 6090. The image data from intraocular device 60 provide information regarding the gaze direction of the subject, and based on that information, the image captured by imaging device 4080 is processed (e.g., cropped) such that a sub-portion of the wide-field image which is in the gaze direction of the subject is included in the processed image. Control circuitry 6070 transmits data based on the processed image to driving circuitry 6080, which in turn drives electrodes 6060 to apply currents to retina 16.

Typically, the processed image that is derived from the extraocular imaging device 4080 is of a wider field of view and/or of higher quality than that available based on data from photosensor array 6050 in intraocular device 60.

Reference is still made to FIG. 3. For some applications, IR transmitter 4024 and data transmitter 4034 are a common element, configured to transmit both (a) data representative of an image and (b) power for operation of intraocular device 60. Typically, for such applications, IR beam 26 is modulated by a suitable modulation protocol to transmit data representative of the image captured by imaging device 4080, in addition to power. Additionally, for such applications, energy receiver 6020 and data receiver 6030 are a common element.

Figure 4A:
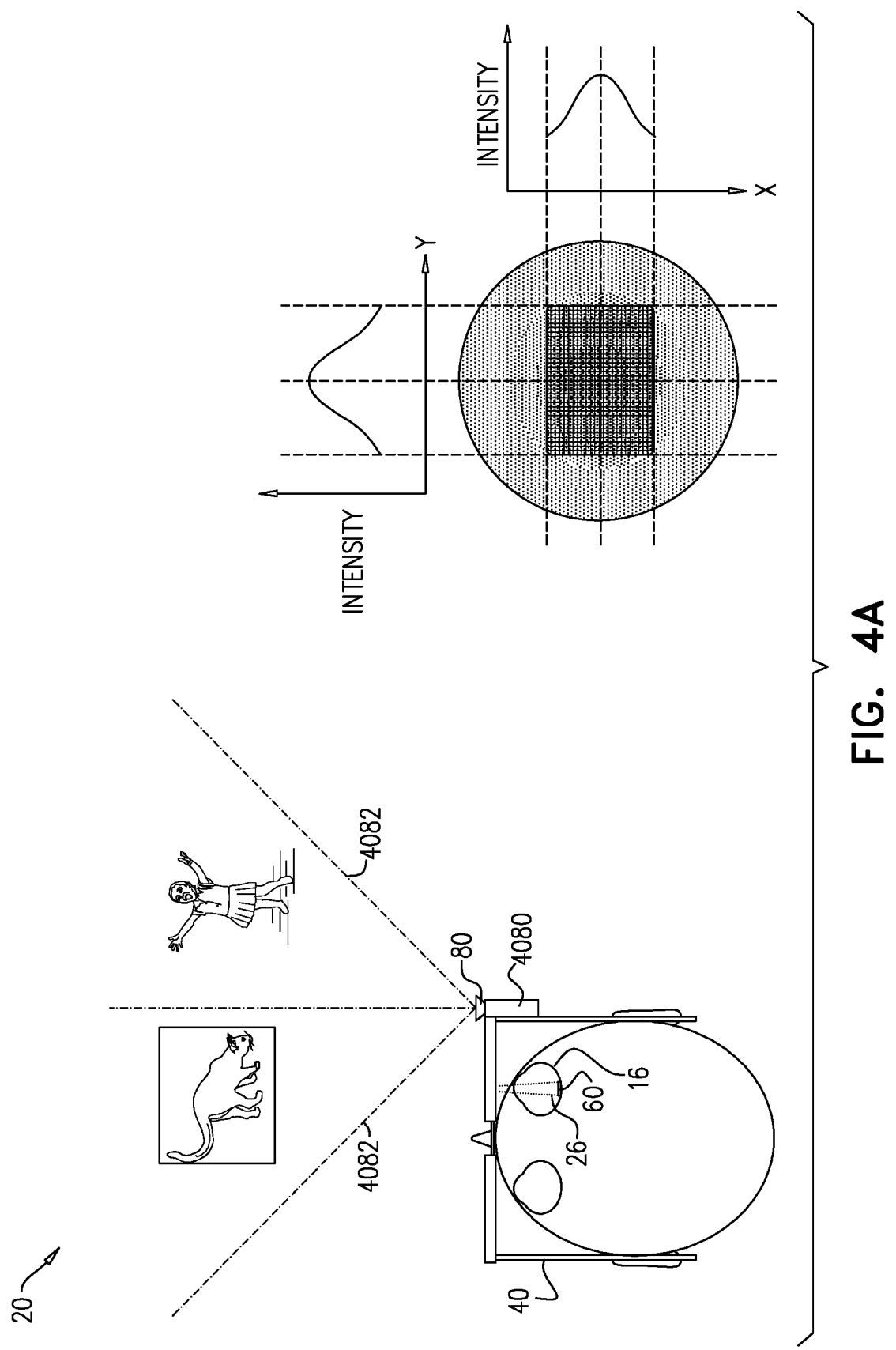
FIGS. 4A-B are schematic illustrations of apparatus for restoring at least partial vision in a subject, in accordance in accordance with some applications of the present invention.
Figure 4B:
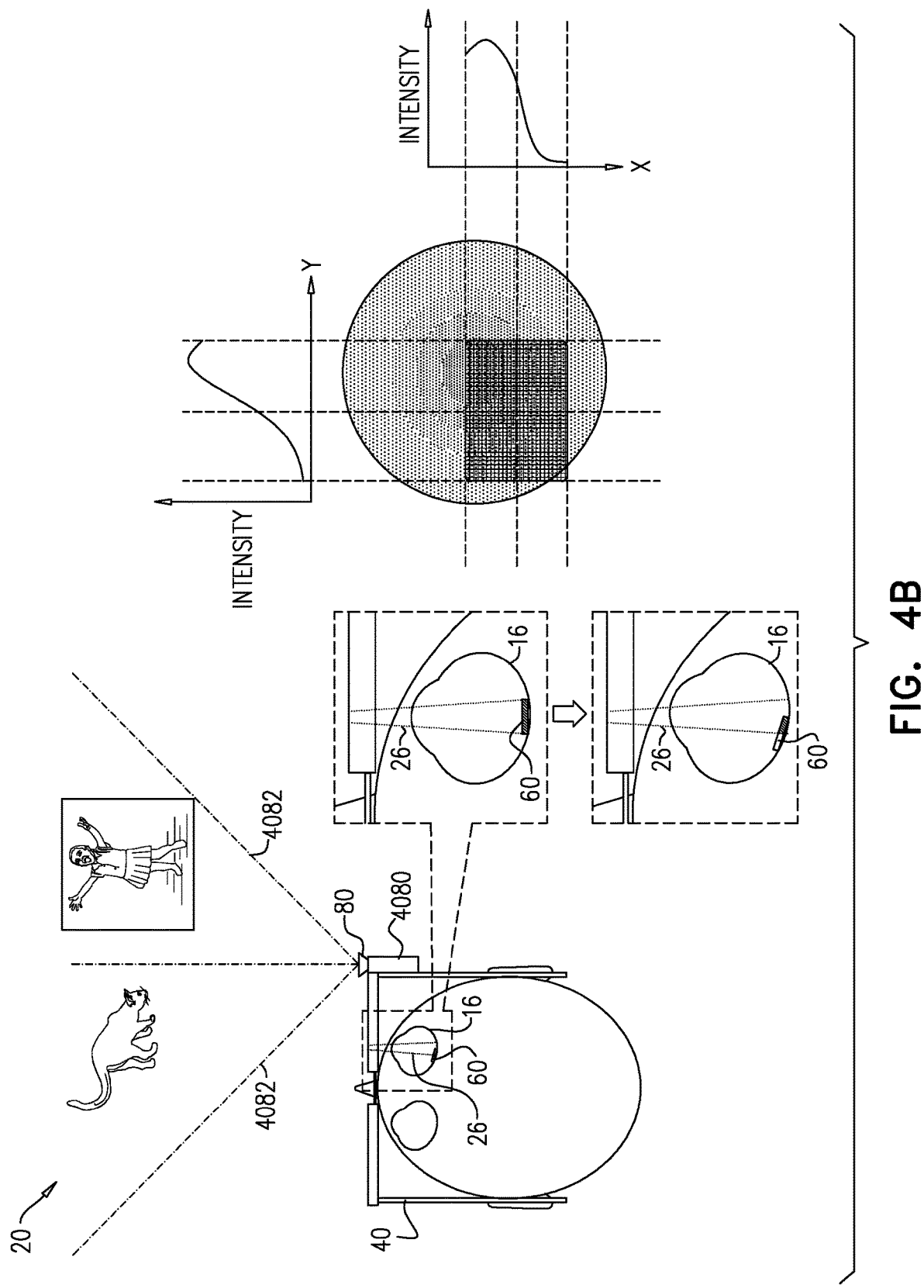

Reference is now made to FIGS. 4A-B and 5. In the applications shown in FIGS. 4A-B and 5, apparatus 20 detects a gaze direction of the subject based on a manner in which non-visible light beam 26 from IR transmitter 4024 is received by intraocular device 60.

Components of extraocular device 40 shown in FIGS. 4A-B and 5 are generally analogous to those already described herein with reference to FIGS. 2A-B and 3, except as described hereinbelow. As shown, extraocular device 40 comprises imaging device 4080 which typically captures a wide field of view (FOV) that is in the subject's environment (indicated by rays 4082 in FIGS. 4A-B). Imaging device 4080 is coupled to eyeglass 4022, which are placed in front of the eye of the subject.

Additionally, coupled to eyeglass 4022, is IR transmitter 4024 which emits non-visible infrared light beam 26 toward eye 28. IR transmitter 4024 is typically fixed to eyeglass 4022 in a known location with respect to imaging device 4080. Infrared light beam 26 emitted from IR transmitter 4024 is used to power the components of intraocular device 60. Typically, infrared light beam 26 is a non-uniform light source having a stable intensity profile; for example, infrared light beam 26 may be brighter at the center than at the edges. It is noted that typically the infrared light emitted from IR transmitter 4024 does not contain data representative of an image. (For applications in which IR transmitter 4024 and data transmitter 4034 are a common element, however, the infrared light emitted from IR transmitter 4024 typically contains data representative of an image.)

Intraocular device 60 illustrated in FIGS. 4A-B typically comprises energy receiver 6020 configured to receive infrared light beam 26 from IR transmitter 4024. Intraocular device 60 further comprises a voltage regulator 6022 configured to maintain a generally constant voltage level to power the components of intraocular device 60.

Intraocular device 60 additionally comprises photosensor array 6052. Since intraocular device 60 is fixed to retina 16, photosensor array 6052 moves in correspondence with movements of eye 28. Additionally, photosensor array 6052 is typically sensitive to infrared light beam 26 from IR transmitter 4024. Unlike photosensor array 6050 described herein with reference to FIGS. 2A-B and FIG. 3, photosensor array 6052 is generally not sensitive to visible ambient light and does not capture an ambient image in the subject's environment. Instead, light beam 26 from IR transmitter 4024 reaches photosensor array 6052, and photosensor array 6052 generates a signal in response to a parameter of the beam of light, the parameter being indicative of a gaze direction of the subject, as described hereinbelow. Based on the indication of the gaze direction of the subject, the wide-field image captured by external imaging device 4080 is cropped to include a sub-portion of the wide-field image (the sub-portion corresponding to an image that is in the gaze direction of the subject).

For some applications, the parameter of light beam 26 comprises an intensity of light beam 26. IR sensitive photosensor array 6052 receives light beam 26, and generates a signal in response to an intensity profile of light beam 26. The signal generated by photosensor array 6052 is processed by intraocular control circuitry 6070 to determine the position of intraocular device 60 with respect to IR transmitter 4024. Based on determining the position of intraocular device 60 with respect to IR transmitter 4024, the direction of the gaze of the subject is established and the image captured by imaging device 4080 is processed. For example, FIG. 4A shows a Gaussian curve graph representing the distribution of light beam 26 from IR transmitter 4024 when intraocular device 60 is centered with light beam 26. In such cases the Gaussian peak is measured in the center of the X and Y axes of the photosensor array 6050. In FIG. 4B, eye 28 is rotated such that the measured Gaussian peak shifts in the X and Y axes. By measuring the shift of the peak (or the profile curve in general) in the X and Y axes, the position of the implant can once again be evaluated relative to the beam.

FIG. 5 is a block diagram of the transmission of energy and image data between extraocular device 40 and intraocular device 60 in accordance with some applications of the present invention. Extraocular device 40 is typically powered by an external power source 4030, e.g., a battery. Extraocular device 40 comprises imaging device 4080 which is configured to capture a wide field of view (FOV). Extraocular device 40 additionally comprises a power source, shown as a non-visible light source, such as IR transmitter 4024. IR transmitter 4024 is typically a laser which emits beam of light 26 to power components of intraocular device 60. Beam of light 26 is typically outside of the visible light range, e.g., outside 380-750 nm. Beam of light 26 transmitted to intraocular device 60 is received by energy receiver 6020. Intraocular device 60 additionally comprises a voltage regulator 6022 configured to maintain a constant voltage level to power the components of intraocular device 60.

As described with references to FIGS. 4A-B, intraocular device 60 further comprises photosensor array 6052, which comprises a plurality of photosensors. Photosensor array 6052 receives light beam 26, and generates a signal in response to an intensity profile of light beam 26. The signal generated by photosensor array 6052 is processed by intraocular control circuitry 6070 to determine the position of intraocular device 60 with respect to IR transmitter 4024. The data from intraocular control circuitry 6070 is transmitted upstream to extraocular device 40 via data transmitter 6040 to data receiver 4036 in extraocular device 40. The data received by data receiver 4036 are transferred to processing circuitry 4074 (extraocular control circuitry 4070 and image processor 4072). Image processor 4072 processes the image captured by imaging device 4080, based on the information from intraocular device 60 with regard to the gaze direction of the subject (that was determined based on determining the position of intraocular device 60 with respect to IR transmitter 4024), and the image captured by imaging device 4080 is cropped such that a sub-portion of the wide-field image which is in the gaze direction of the subject is included in the image. The processed image is transmitted back to intraocular device 60 via data transmitter 4034 and received in intraocular device 60 by data receiver 6030 and intraocular control circuitry 6070. Control circuitry 6070 generates a signal in response to the received processed image, and the signal is transmitted to driving circuitry 6080, which drives the electrode 6060 to apply currents to retina 16.

Reference is still made to FIG. 5. For some applications, total image data of the image captured by extraocular imaging device 4080 are transmitted downstream to intraocular device 60 via data transmitter 4034, for processing by intraocular processing circuitry 6074 in accordance with the position and orientation of intraocular device 60 with respect to IR transmitter 4024. That is, the image captured by imaging device 4080 is processed (e.g., cropped) such that a sub-portion of the wide-field image which is in the gaze direction of the subject is included in the processed image. Control circuitry 6070 transmits data based on the processed image to driving circuitry 6080, which in turn drives electrodes 6060 to apply currents to retina 16.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
   (A) an intraocular device configured to be implanted entirely in a subject's eye, the intraocular device comprising:
      an energy receiver configured to receive light to power the intraocular device;
      a plurality of stimulating electrodes;
      an array of photosensors, each photosensor configured to detect photons representing an image in a gaze direction of the subject, and to generate a signal in response thereto; and
      driving circuitry configured to utilize energy from the energy receiver to drive the electrodes to apply currents to a retina of the subject's eye;
   (B) an extraocular device comprising:
      an eyeglasses frame, configured to be placed in front of the subject's eye;
      a non-visible light source coupled to the eyeglasses frame and configured to transmit light to the energy receiver;
      an imaging device coupled to the eyeglasses frame and configured to capture a wide-field image; and
   (C) processing circuitry configured to (i) receive the wide-field image from the imaging device, (ii) based on the signal from the photosensors, process the wide-field image from the imaging device to generate image data representative of a sub-portion of the wide-field image, and (iii) cause the driving circuitry to drive the electrodes to apply currents to the retina based on the image data.

2. The apparatus according to claim 1, wherein the extraocular device is configured to modulate the light emitted from the non-visible light source to contain data representative of the image captured by the imaging device.

3. The apparatus according to claim 1, wherein the imaging device comprises a wide-angle lens.

4. The apparatus according to claim 1, wherein the imaging device is configured to capture a field of view that is larger than a field of view detected by the array of photosensors.

5. The apparatus according to claim 4, wherein the imaging device is positioned with respect to the eyeglasses frame such that when the subject wears the eyeglasses frame, the image detected by the array of photosensors is a sub-portion of the wide-field image captured by the imaging device.

6. The apparatus according to claim 1, wherein the sub-portion of the wide-field image generated by the processing circuitry is derived from a field of view that is larger than a field of view detected by the array of photosensors.

7. The apparatus according to claim 1, wherein the intraocular device further comprises an image processor, configured to extract one or more principle features of the image detected by the array of photosensors, and wherein the processing circuitry is configured to generate the image data representative of the sub-portion of the wide-field image based on the extracted principle features of the image detected by the array of photosensors.

8. The apparatus according to claim 1, wherein the extraocular device comprises the processing circuitry and is configured to transmit the image data representative of the sub-portion of the wide-field image to the intraocular device to cause the driving circuitry to drive the electrodes to apply currents to the retina based on the image data.

9. The apparatus according to claim 1, wherein the intraocular device comprises the processing circuitry.

10. Apparatus, comprising:
    (A) an extraocular device, comprising:
       an eyeglasses frame, configured to be placed in front of an eye of a subject;
       a non-visible light source coupled to the eyeglasses frame and configured to emit toward the eye a beam of light that (i) is outside of 380-750 nm, and (ii) does not contain data representative of an image; and
       an imaging device coupled to the eyeglasses frame and configured to capture a wide-field image;
    (B) an intraocular device configured to be implanted entirely in the subject's eye, the intraocular device comprising:
       an energy receiver, configured to receive the beam of light from the non-visible light source to power the intraocular apparatus;
       a plurality of stimulating electrodes;
       driving circuitry configured to utilize energy from the energy receiver to drive the electrodes to apply currents to a retina of the subject's eye; and
       an array of photosensors, configured to receive the beam of light from the power source and to generate a signal in response to a parameter of the beam of light, the parameter being indicative of a gaze direction of the subject; and
    (C) processing circuitry configured to (i) receive the wide-field image from the imaging device, (ii) based on the signal from the photosensors, process the wide-field image from the imaging device to generate image data representative of a sub-portion of the wide-field image, the sub-portion corresponding to an image that is in the gaze direction of the subject and (iii) cause the driving circuitry to drive the electrodes to apply currents to the retina based on the image data.

11. The apparatus according to claim 10, wherein the extraocular device comprises the processing circuitry and is configured to transmit the image data representative of the sub-portion of the wide-field image to the intraocular device to cause the driving circuitry to drive the electrodes to apply currents to the retina based on the image data.

12. The apparatus according to claim 10, wherein the intraocular device comprises the processing circuitry.

13. The apparatus according to claim 10, wherein the imaging device comprises a wide-angle lens.

14. The apparatus according to claim 10, wherein the array of photosensors are generally insensitive to visible light.

15. The apparatus according to claim 10, wherein the parameter of the beam of light comprises an intensity of the beam of light, and wherein the photosensor array is configured to generate a signal in response to the intensity of the beam of light received by the photosensor array.

* * * * *